(12) United States Patent
McDonald

(10) Patent No.: US 7,153,316 B1
(45) Date of Patent: Dec. 26, 2006

(54) SURGICAL INSTRUMENTS AND METHOD FOR CORNEAL REFORMATION

(76) Inventor: Marguerite B. McDonald, 2858 Chestnut St., New Orleans, LA (US) 70115

( * ) Notice: Subject to any disclaimer, the term of this patent is extended or adjusted under 35 U.S.C. 154(b) by 380 days.

(21) Appl. No.: 10/014,373

(22) Filed: Nov. 9, 2001

(51) Int. Cl.
*A61F 9/007* (2006.01)

(52) U.S. Cl. ............... 606/166; 606/190; 604/264

(58) Field of Classification Search ......... 604/264, 604/272; 606/166, 190
See application file for complete search history.

(56) References Cited

U.S. PATENT DOCUMENTS

| | | | |
|---|---|---|---|
| 10,303 A | 12/1853 | Warren | |
| 634,108 A | 10/1899 | Henry | |
| 762,603 A | 6/1904 | Witkowski | |
| 1,125,887 A | 1/1915 | Schimmel | |
| 1,331,271 A | 2/1920 | MacGregor | |
| 1,569,174 A | 1/1926 | Crowther | |
| 3,439,675 A | 4/1969 | Cohen | 128/239 |
| 3,661,144 A | 5/1972 | Jensen et al. | 128/2 B |
| 4,190,050 A | 2/1980 | Bailey | 128/305 |
| 4,432,758 A | 2/1984 | Finegold | 604/104 |
| 4,524,771 A * | 6/1985 | McGregor et al. | 606/223 |
| 4,617,018 A | 10/1986 | Nishi | 604/264 |
| 4,798,599 A | 1/1989 | Thomas | 604/290 |
| 4,813,928 A | 3/1989 | Abe et al. | 604/49 |
| 5,217,465 A | 6/1993 | Steppe | 606/107 |
| 5,234,436 A | 8/1993 | Eaton et al. | |
| 5,263,950 A | 11/1993 | L'Esperance, Jr. | 606/6 |
| 5,275,607 A | 1/1994 | Lo et al. | 606/169 |
| 5,356,389 A | 10/1994 | Willing | 604/164 |
| 5,405,355 A | 4/1995 | Peyman et al. | |
| 5,423,764 A | 6/1995 | Fry | 604/187 |

(Continued)

FOREIGN PATENT DOCUMENTS

WO  WO 01/28473 A  4/2001

(Continued)

OTHER PUBLICATIONS

EPO, Communication Pursuant to Article 96(2) EPC, App. No. 04 028 324.4-2305 (Nov. 04, 2006).

(Continued)

*Primary Examiner*—Michael Thaler
(74) *Attorney, Agent, or Firm*—W. Edward Ramage; Baker Donelson Bearman Caldwell & Berkowtiz, P.C.

(57) ABSTRACT

A surgical method of corneal reformation reduces the risk of trauma and shortens overall recovery while yielding improved visual acuity includes making a relatively shallow incision of no more than about 85 microns deep into the corneal epithelium, separating the corneal epithelial sheet from the underlying Bowman's Membrane using an epithelial separator or a specialized cannula, and lifting the epithelial sheet away from the ablation zone so that the Bowman's Membrane and underlying stromal bed can be reformed. Multiple surgical instruments include the optional use of vibration with an epithelial separator or cannula to separate an epithelial sheet from the cornea of no more than about 85 microns thick.

12 Claims, 8 Drawing Sheets

U.S. PATENT DOCUMENTS

| | | |
|---|---|---|
| 5,632,757 A | 5/1997 | Arnott |
| 5,755,700 A | 5/1998 | Kritzinger et al. ........... 604/257 |
| 5,792,099 A | 8/1998 | DeCamp et al. .............. 604/51 |
| 5,800,406 A | 9/1998 | Kritzinger et al. .......... 604/257 |
| 5,817,075 A | 10/1998 | Giungo ....................... 604/294 |
| 5,876,379 A | 3/1999 | Beauvais et al. ........... 604/181 |
| 5,989,272 A | 11/1999 | Barron et al. |
| 5,997,516 A | 12/1999 | Caro et al. .................. 604/264 |
| 6,024,726 A | 2/2000 | Hill ............................. 604/187 |
| 6,030,393 A * | 2/2000 | Corlew ....................... 606/148 |
| 6,042,572 A | 3/2000 | Fowler ....................... 604/239 |
| 6,047,209 A | 4/2000 | Denny et al. ................. 604/21 |
| 6,135,984 A | 10/2000 | Dishler ....................... 604/264 |
| 6,413,245 B1 | 7/2002 | Yaacobi et al. |
| 6,443,944 B1 * | 9/2002 | Doshi et al. .................... 606/1 |
| 6,562,020 B1 * | 5/2003 | Constantz et al. .......... 604/523 |
| 2002/0116020 A1 | 8/2002 | Kurenkov |

FOREIGN PATENT DOCUMENTS

WO      WO 01/56520 A      8/2001

OTHER PUBLICATIONS

EPO, Communication Pursuant to Article 96(2) EPC, App. No. 02 257 715.9-2305 (Dec. 04, 2006).

* cited by examiner

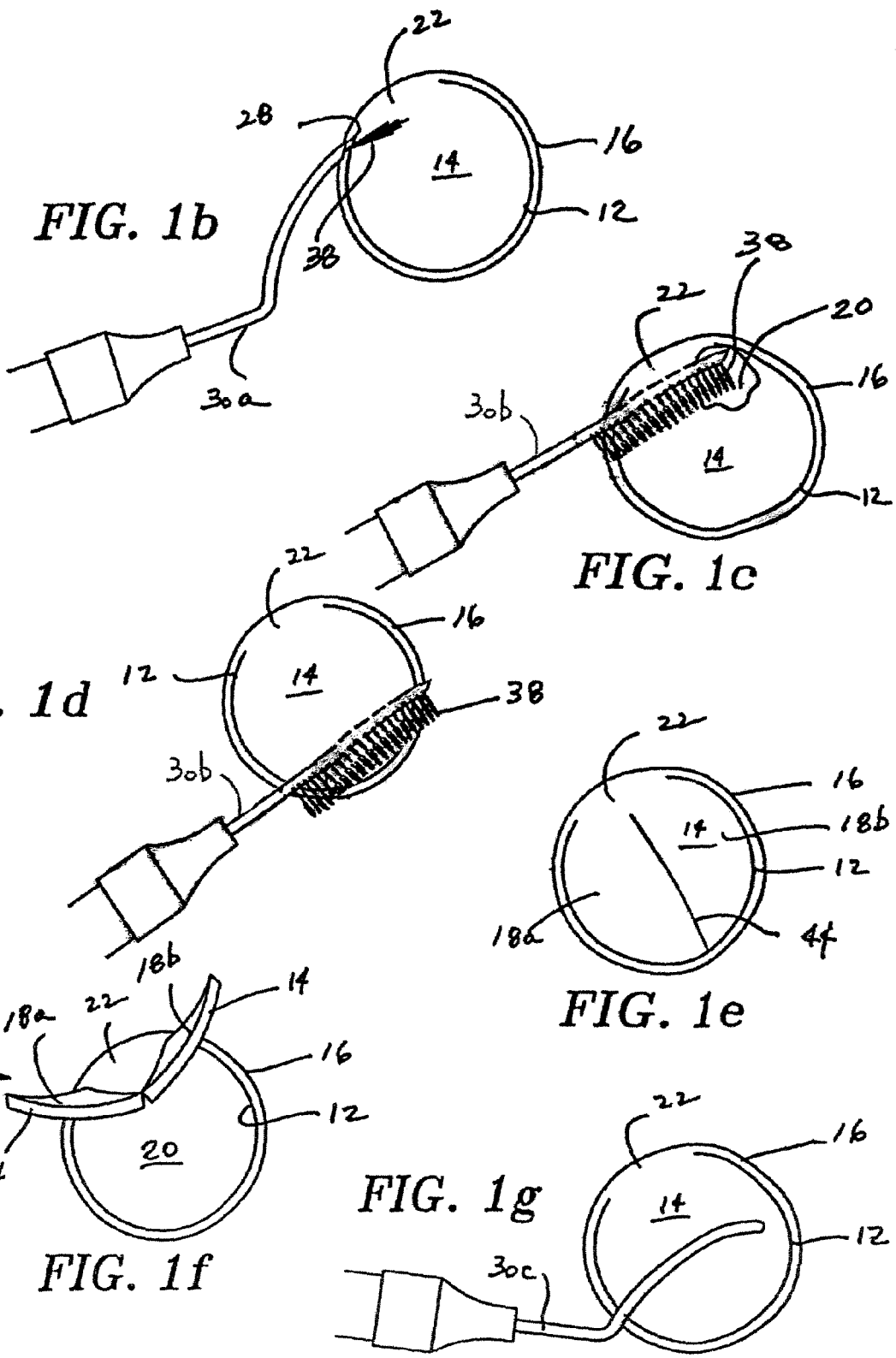

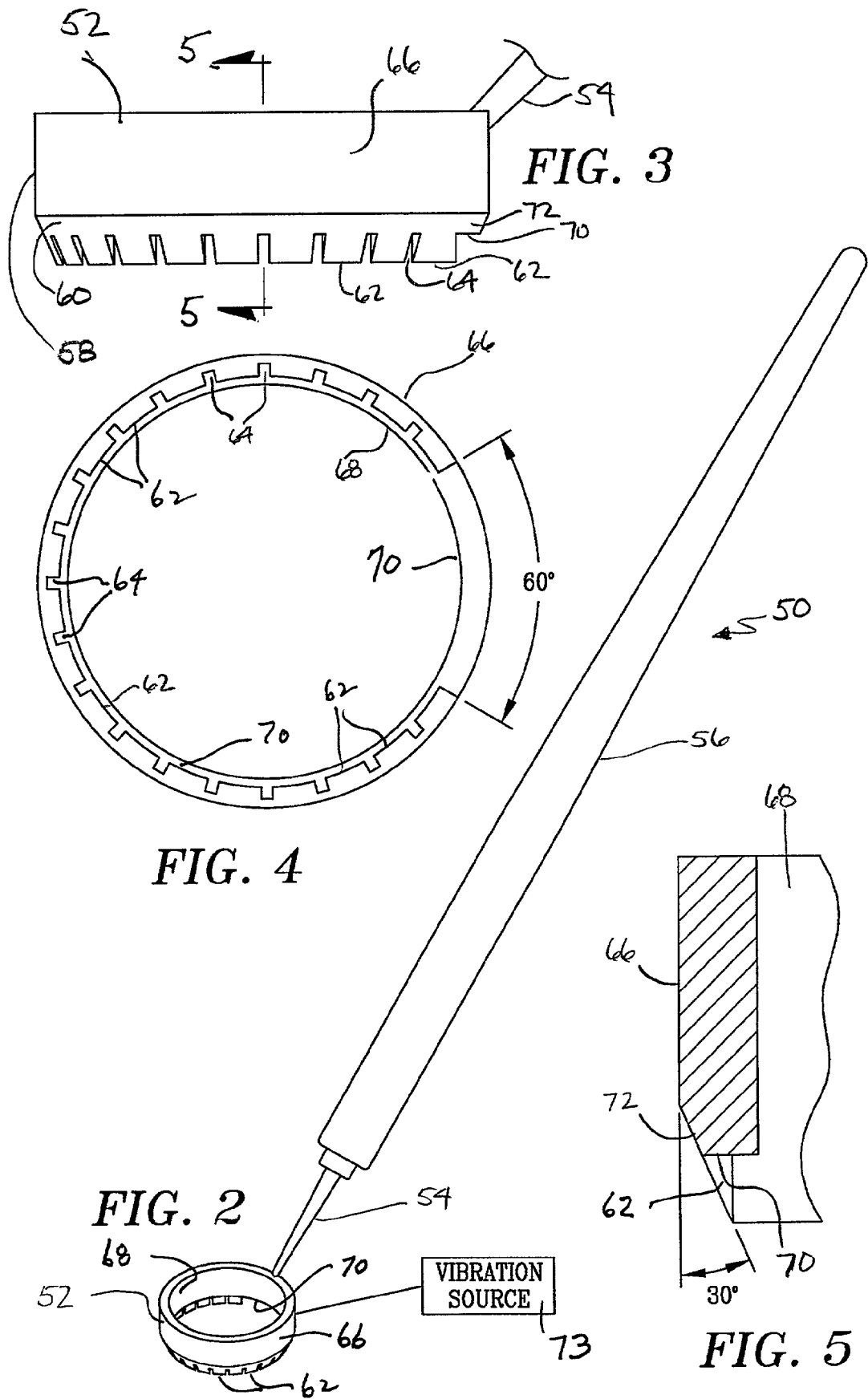

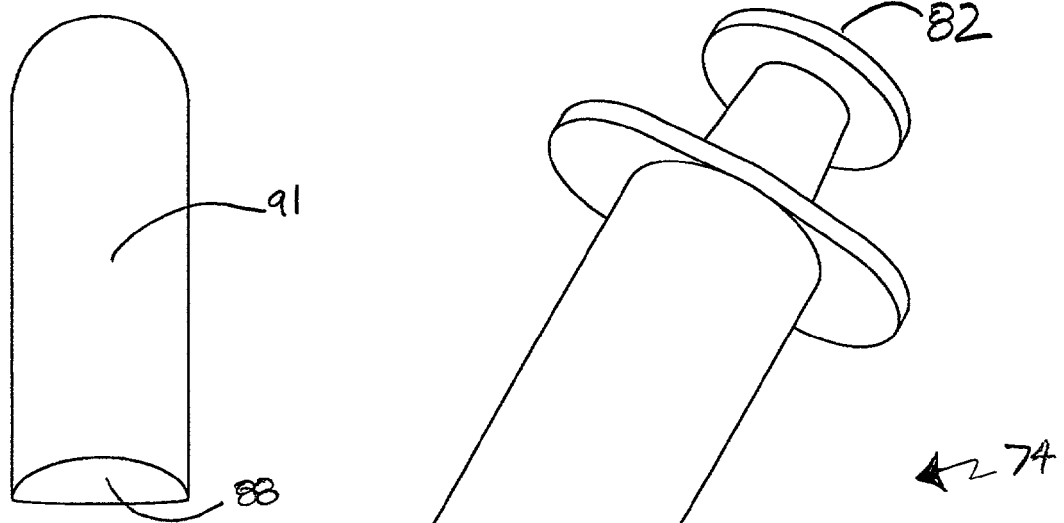
FIG. 9
FIG. 6
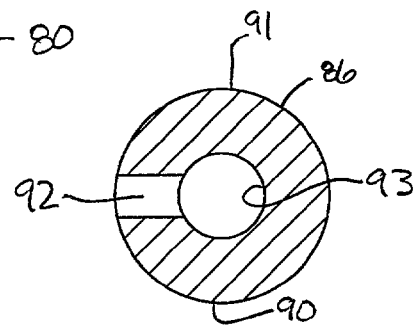
FIG. 8
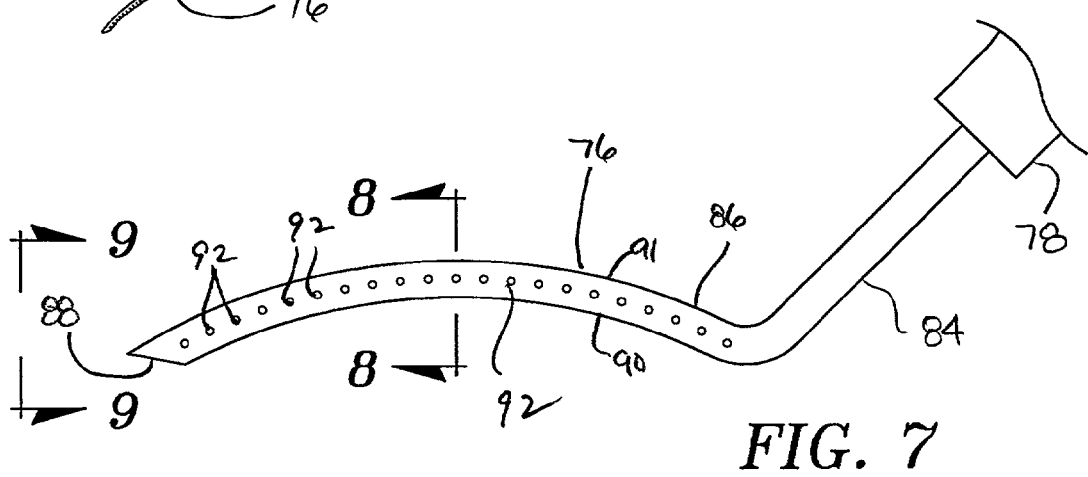
FIG. 7

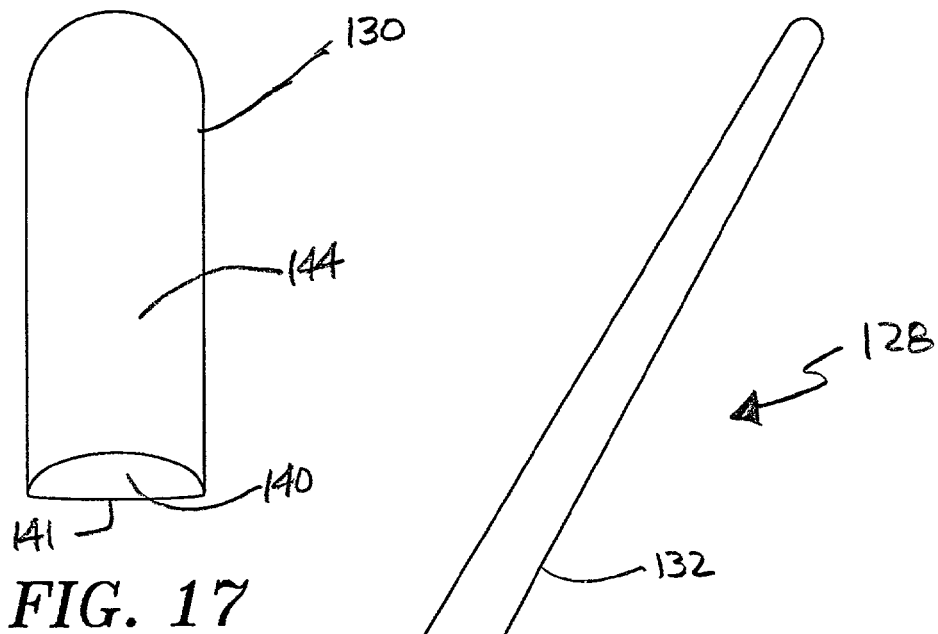
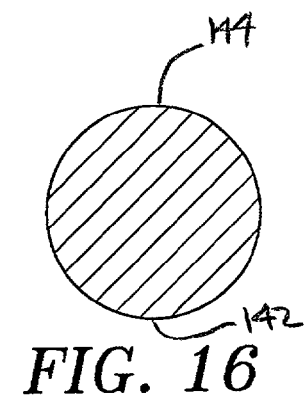
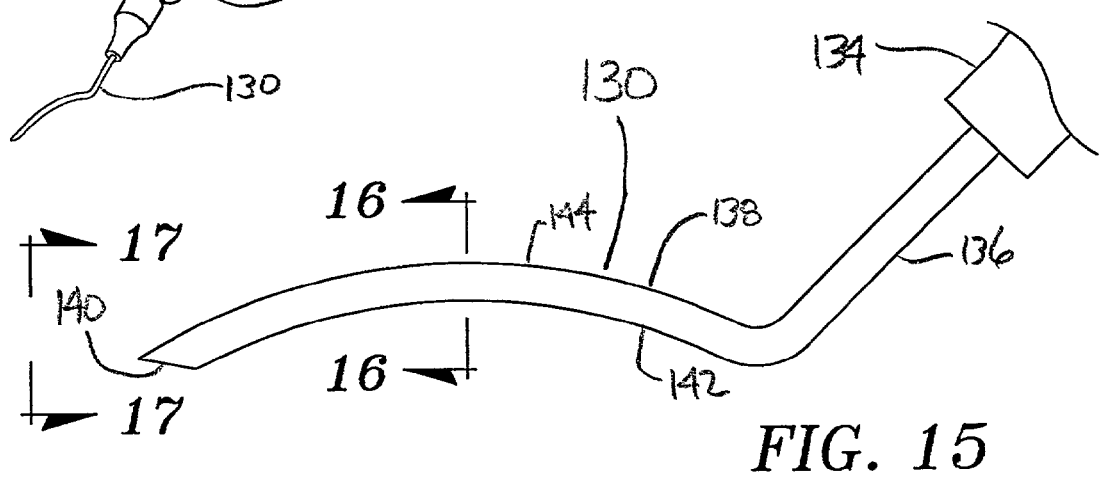
FIG. 17
FIG. 14
FIG. 16
FIG. 15

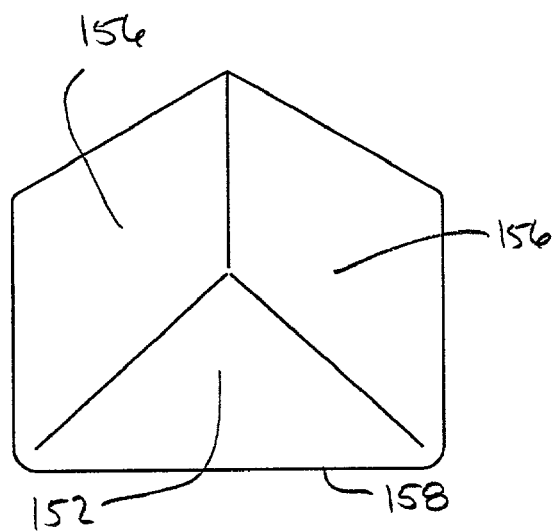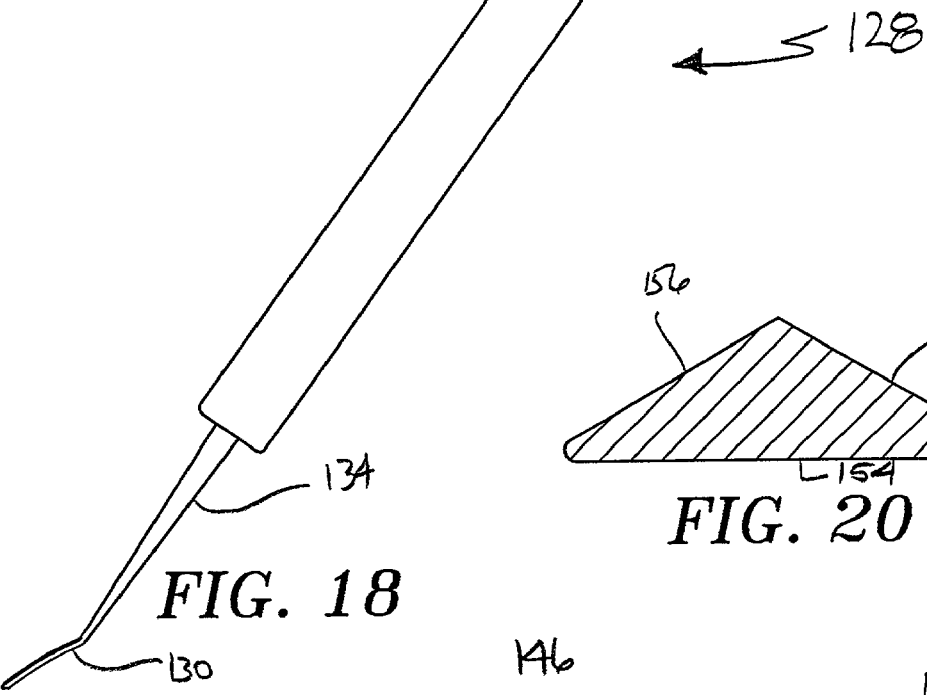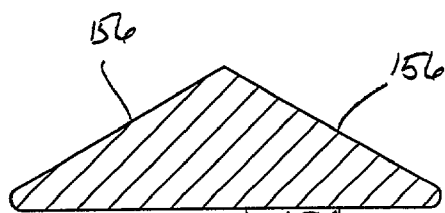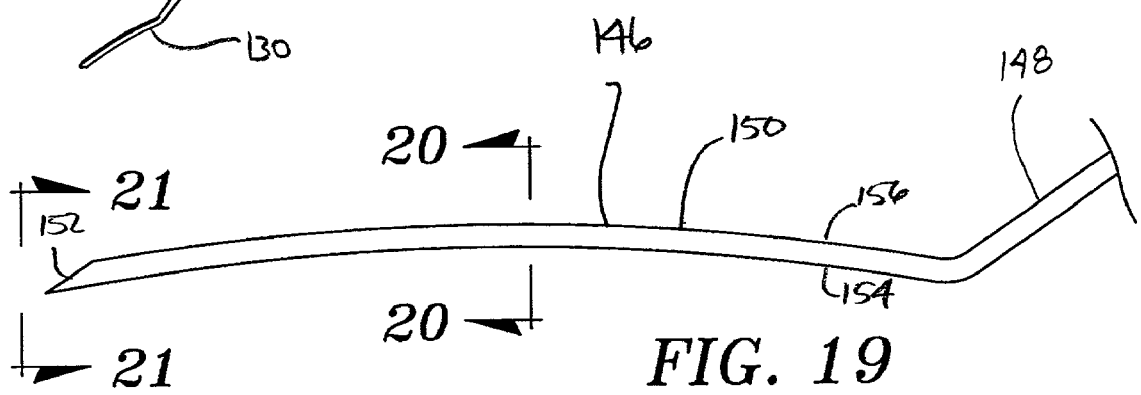
FIG. 21
FIG. 18
FIG. 20
FIG. 19

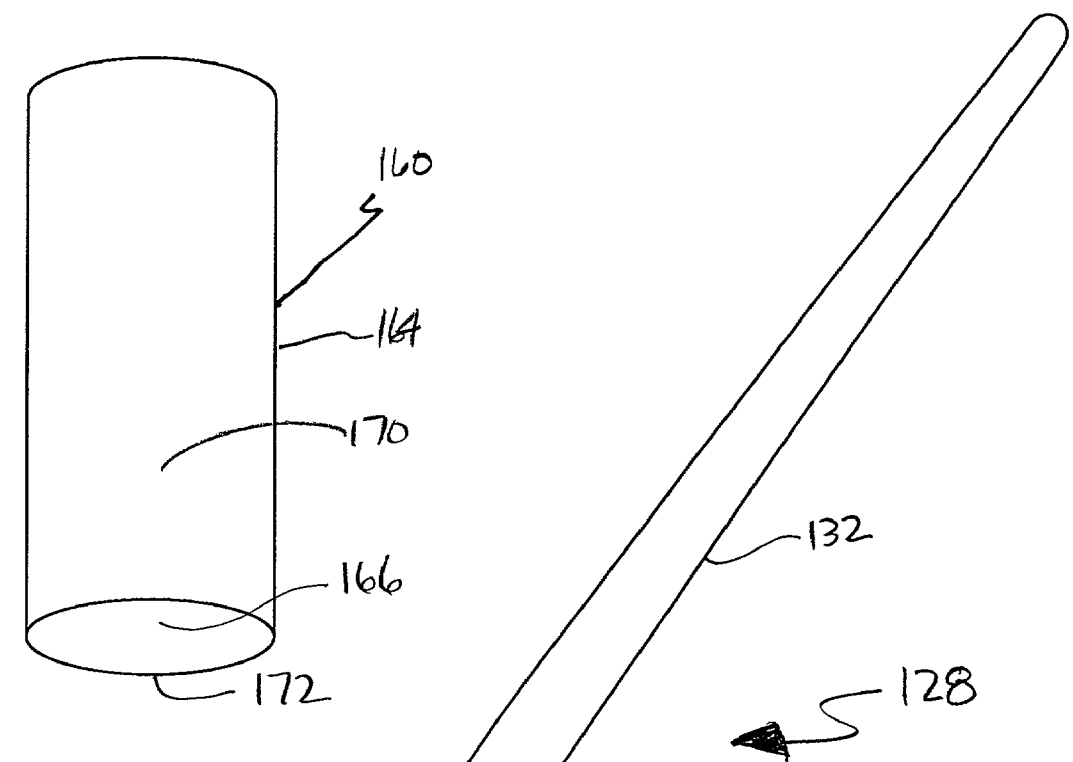
FIG. 25
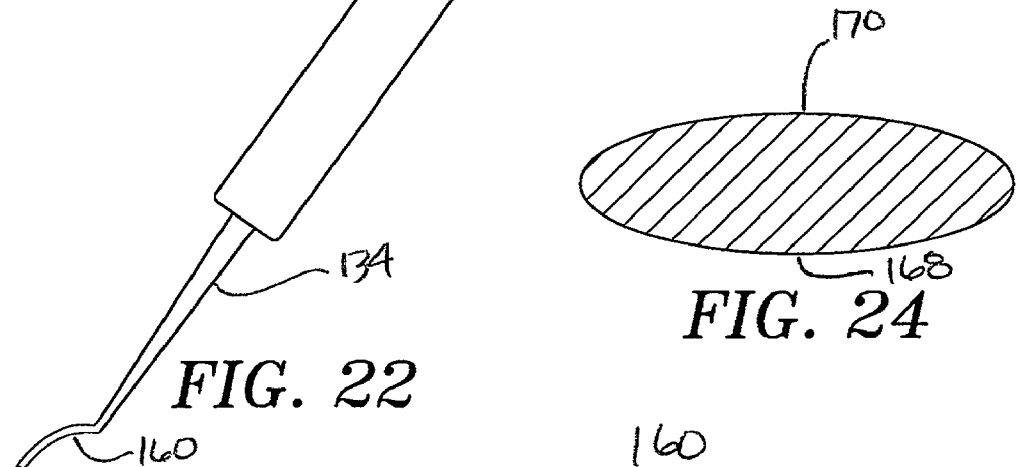
FIG. 22
FIG. 24
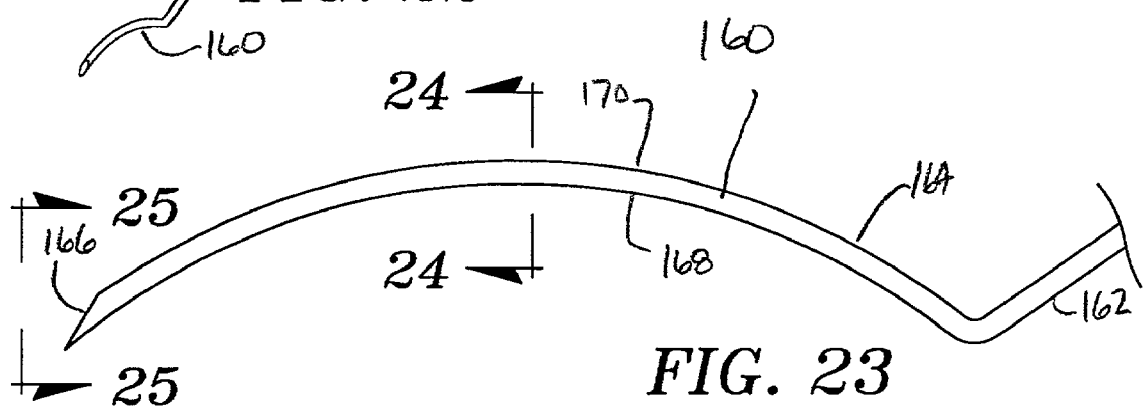
FIG. 23

SURGICAL INSTRUMENTS AND METHOD FOR CORNEAL REFORMATION

TECHNICAL FIELD OF THE INVENTION

The present invention relates to methods for corneal reformation, specifically, to a method for corneal reformation that permits faster recovery with improved visual acuity and surgical instruments for performing such methods.

BACKGROUND OF THE INVENTION

The human eye includes a specialized structure referred to as the cornea. The cornea is a multi-layered structure, however, the three most superficial layers—the corneal epithelium, Bowman's Membrane, and the stromal bed—are the layers that are primarily implicated in corneal reformation surgery. The epithelium, which comprises the delicate covering of the human cornea and is only five or six cells thick, is the protective barrier against infection of the cornea. The cornea, being avascular, has unique immune requirements and an infection in this part of the eye is problematic since systemic antibiotics are relatively ineffective. Therefore, preservation of the epithelial integrity is critical in surgery as well as for general eye care.

The epithelium is adherent to the stromal surface along Bowman's Membrane which is a cell-free zone approximately 7 to 12 microns thick and defines the Basement Membrane. Bowman's Membrane is the most anterior structure of the stromal tissue which is the major lamellar structure of the corneal anatomy. In most surgeries of the cornea, efforts are made to prevent the tearing of the epithelium from Bowman's Membrane because such tearing causes pain, slow visual recovery, and predisposes to corneal infiltrates (precursors to infection).

Some corneal reformation techniques, such as LASIK, require the creation of a flap of corneal epithelium which may result in significant destruction of the stromal bed leading to trauma or even permanent damage to the eyes and compromise eyesight. PRK, on the other hand, removes the upper most layer(s) of corneal epithelium without danger to the underlying stromal bed but requires a long recovery period for the patient.

In LASIK, in order to create a useable flap, the flap must be relatively thick. A thick flap, however, requires corneal reformation by ablating underlying tissue that extends into the stromal bed of the cornea. Ablating this tissue has severe consequences. Unless sufficient tissue remains in the stromal bed, the cornea can destabilize resulting in keratoectasia. A patient's long recovery time after PRK surgery is disadvantageous for multiple reasons, such as lengthier vulnerability to infection, discomfort, and inability to return to daily routine quickly.

Accordingly, there is a need for a method of corneal reformation that reduces the risk of trauma and permanent damages to the eye while permitting quick recovery.

SUMMARY OF THE INVENTION

In accordance with the present invention, a method for reforming the cornea to alter visual acuity is presented whereby a shallow incision of less than about 85 microns is made into the corneal epithelium to create a sheet of epithelium. The sheet of epithelium is separated from the Bowman's Membrane using an epithelial separator or cannula and then is lifted from of the cornea to permit ablation of the underlying membrane followed by return of the epithelial sheet.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which:

FIGS. 1b–1g are pictorial representations illustrating steps of the present method;

FIG. 2 is a perspective view of a trephine used in practicing the present method;

FIG. 3 is a side elevational view of the trephine cutting band illustrated in FIG. 2;

FIG. 4 is a bottom plan view of the trephine cutting band shown in FIG. 3;

FIG. 5 is a sectional view taken generally along sectional lines 5—5 of FIG. 3 of the trephine cutting band;

FIG. 6 is a perspective view of an embodiment of a surgical instrument used in the practice of the present method;

FIG. 7 is an enlarged side elevational view of the cannula shown in FIG. 6;

FIG. 8 is sectional view taken generally along sectional lines 8—8 of FIG. 7 of the cannula of the present invention;

FIG. 9 is a front elevation view taken generally at lines 9—9 of FIG. 7 of the distal tip of the cannula of the present invention;

FIG. 14 is a perspective view of an embodiment of an epithelial separator used in the practice of the present method;

FIG. 15 is an enlarged side elevational view of the spatula-like portion of the epithelial separator shown in FIG. 14;

FIG. 16 is a sectional view taken generally along sectional lines 16—16 of FIG. 15 of the spatula-like portion of the epithelial separator of FIG. 14;

FIG. 17 is a front elevational view taken generally along lines 17—17 of FIG. 15 of the distal tip of the epithelial separator of the present invention shown in FIG. 14;

FIG. 18 is a perspective view of a further embodiment of an epithelial separator used in the practice of the present method;

FIG. 19 is a side elevational view of the spatula-like portion of the epithelial separator shown in FIG. 18;

FIG. 20 is a sectional view taken generally along sectional lines 20—20 of FIG. 19 of the spatula-like portion of the epithelial separator shown in FIG. 18;

FIG. 21 is a front elevational view taken generally along lines 21—21 of FIG. 19 of the distal tip of the spatula-like portion of the epithelial separator of FIG. 18;

FIG. 22 is a perspective view of a further embodiment of an epithelial separator used in the practice of the present method;

FIG. 23 is a side elevational view of the spatula-like portion of the epithelial separator of FIG. 22;

FIG. 24 is a sectional view taken generally along sectional lines 24—24 of FIG. 23 of the spatula-like portion of the separator shown in FIG. 22; and FIG. 25 is a front elevational front view taken generally along lines 25—25 of FIG. 23 of the distal tip of the spatula-like portion of the epithelial separator of FIG. 22.

DESCRIPTION OF THE PREFERRED EMBODIMENTS

Figure 1A:
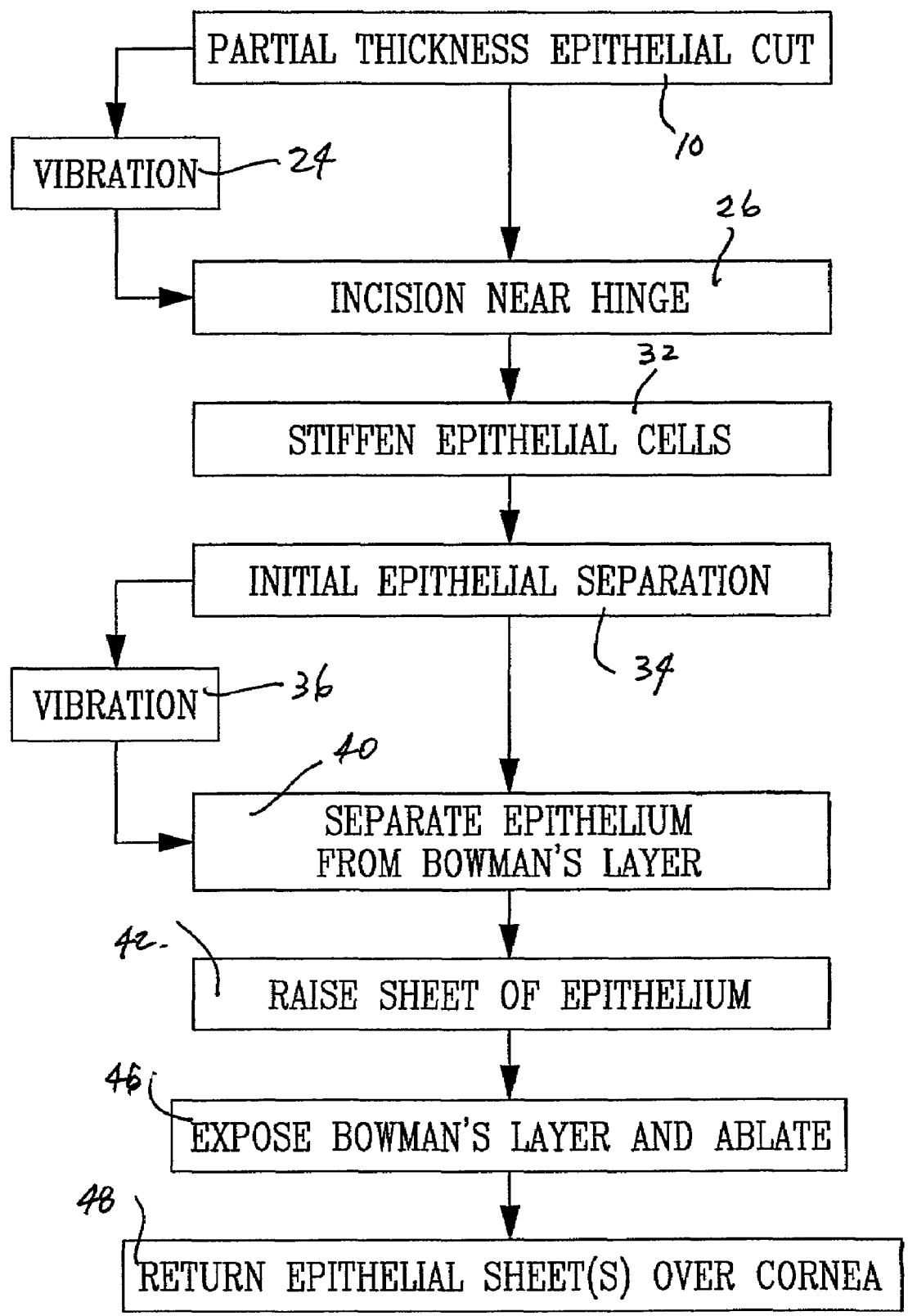
FIG. 1a is a block diagram illustrating the present method.

The present method for reforming the corneal surface of the mammalian eye has advantages of LASIK surgery while avoiding the disadvantages of PRK surgery. The present method is termed LASEK. Briefly, in practicing LASEK a gossamer thin sheet of no more than about 85 microns of the corneal epithelium is lifted from the corneal surface to permit corneal reformation of the underlying epithelium and is then replaced. The present method permits rapid recovery like LASIK. With the present method, the corneal bed is mostly maintained which prevents thickening or other indications of trauma. Another advantage of the present invention is that, unlike PRK, the eye is not treated with harsh chemicals that are used in PRK to remove the corneal epithelium and long recovery periods are avoided. Again, by reducing the cornea's exposure to irritants, damage to the cornea is avoided and recovery time is enhanced.

Referring to FIGS. 1a–1g, a block diagram of the present method is illustrated together with pictorial representations of steps of the present method. At step 10, a full or partial thickness epithelial cut 12 is made in the epithelial layer 14 of cornea 16 of an eye. This incision 12 is no deeper than about 85 microns. The incision 12 forms a sheet 18 (FIG. 1f) that can be lifted from the underlying Bowman's Membrane 20. The area 22 of the cornea 16 and surrounding area that remains attached to the underlying corneal epithelium 14 is termed the "hinged region" as this region functionally serves as a hinge whereby the sheet 18 is maintained attached to the epithelium 14. In a preferred embodiment of the invention, a curved, "C"-shaped, partial or full depth epithelial incision 12 is made to form an arc of between about 250 and 330 degrees. This incision 12 is preferably made using a guarded trephine, to be subsequently described with respect to FIG. 2 which may be vibrated at step 24. An example of a trephine is illustrated in FIG. 2 for making an incision 12 of about 300 degrees. The incision 12 can alternatively be made by a variety of surgical tools such as a scalpel or knife.

In step 26, an incision 28 using a scalpel or similar cutting instrument, preferably with a rounded blade, is made near the hinge 22 of the partial thickness epithelial cut 12. This incision 28 is about 1 to about 2 millimeters long and is sufficiently deep to reach the corneal bed, stromal layer, or Bowman's Membrane 20 and is about 1 to about 2 millimeters long. A cutting instrument 30a for performing step 26 is illustrated in FIG. 3a. Cut 28 may be made using a fluid 38 expelled from the tip of instrument 30a.

In step 32 of the present invention, the epithelial cells are stiffened by adding several drops of sodium chloride in a concentration ranging from about 3% to about 7% (such as Muro 128) for 10 seconds followed by rinsing with buffered saline solution. Stiffening of the epithelial cells makes them easier to handle.

After the incision 28 is made in step 26, the epithelium layers remain firmly affixed to each other. To separate the corneal epithelium from the underlying epithelium an epithelial separator, such as instrument 30b, is inserted under the layer 14 near its hinge region 22 at step 34 (FIG. 1c). This insertion is done by entering the incision 28 made in step 26 and is preferably done by applying suction to the eye and using an epithelial separator 30b which may vibrate. Suction should last for no longer than about 45 seconds and, if necessary, should only be tried a second time after about 15 seconds has elapsed since the first attempt. Suction may not be necessary, however, when vibration is used at step 36. Instead of using an epithelial separator, a cannula capable of ejecting media 38 may be used to enter the incision 28 created at step 26. A more detailed description instruments 30a–c and manners of use are described in more detail below. An epithelial separator is contemplated to be no greater than about one-half millimeter in diameter which permits its entry under the epithelium without tearing what will become the sheet. The epithelial separator is inserted parallel to hinge 22 connecting the ends of the incision line or lines, whereby hinge 22 substantially marks the attachment boundary or hinge 22 of the sheet 18 after the epithelium 14 is lifted.

Once the epithelial separator 30b is inserted at or near the hinge region, the separator 30b is slid away from the hinge region 22 while being held substantially perpendicularly to the direction of movement and parallel to the uncut line at step 40 (FIG. 1d). During step 40 the epithelial layers are teased apart by a gentle sawing, "window washing" motion. Alternatively, a cannula having an internal cavity and having one side having a plurality of apertures is contemplated whereby a medium such as gel, liquid, or gas (including air) 38, hereinafter collectively referred to by the term "fluid", can be used to tease the epithelial layers apart and to raise the epithelial layer. A more detailed description of this embodiment of the cannula will be also discussed below.

After the epithelial separator or cannula 30b is slid along under the corneal surface within the incision area created by cut 12 the epithelium layers are separated to form sheet 18 at step 42. If the corneal area to be altered is relatively large, the sheet 18 may be bisected (FIG. 1e) by making an incision 44 in the epithelium sheet to form two halves 18a and 18b, or leafs, which may be more easily moved out of the ablation zone. Additional leafs may be created depending on the size of the corneal area to be altered.

At step 46, the sheet 18 is lifted from the underlying surface to expose the Bowman's Membrane 20 or bare stoma in a re-treatment case and the corneal bed is ablated or altered by any of a variety of methods commonly known to one of ordinary skill in the art such as by excimer laser and refractive technology.

After ablating the corneal bed, as needed the sheet 18 is replaced over the underlying cornea at step 48 (FIG. 1g) using an instrument 30c to refloat sheet 18 back into position. An instrument 30c is subsequently described with respect to FIGS. 14–25.

Several instruments are used in the practice of the present invention. To make the initial incision 12 (step 10, FIG. 1b) a guarded trephine is preferable such as the one shown in FIG. 2. Guarded trephine generally identified by the numeral 50 includes a cutting member 52, a shaft 54, and a handle 56. Cutting member 52 is shown in greater detail in FIGS. 3–5. Cutting member 52 includes a support band 58, a cutting band 60, cutting teeth 62, spaced apart by gaps 64, an outer surface 66, an inner surface 68, and an edge 70. Cutting teeth 62 may protrude, for example, from cutting band 60 along the innermost about 90 microns leaving the remaining thickness of the outer surface 66 of cutting band 60 to form edge 70. Cutting teeth 62 cut from about 250 to about 330 degrees along the circular cutting band 60 to form hinge region 22 (FIG. 1b), or an uncut arc of the epithelium, of about 110 to about 30 degrees. FIG. 4 illustrates trephine 50 for forming an uncut arc or hinge of about 60 degrees. FIG. 5 is a cross-sectional view of cutting member 52 through the a gap 64 along sectional lines 5—5 in FIG. 3. Shown is inner surface 68, bottom edge 70, and beveled edge 72 of outer surface 66. In a preferred embodiment, beveled edge 72 is angled towards inner surface 68 at about 30 degrees. Additionally, cutting band 60 may include a continuous cutting surface in which gaps 64 have been eliminated.

In a preferred embodiment of trephine 50, cutting member 52 is connected to a vibration source 73. Vibration source 73 may comprise, for example, a mechanical vibrator on an ultra sound vibration source. Vibration is in the range of 20 kHz to 200 kHz. As noted above, the incision made by trephine 50, if approximately circular, and is about 250 to 330 degrees. Trephines for creating cuts of other dimensions are acceptable so long as the cut is partial to leave an area of attachment between the corneal epithelium its surrounding epithelium to form the hinge 22 (FIG. 1b).

To accomplish steps 34 and 40 (FIG. 1a), the separation of the corneal surface epithelium from the underlying cornea several embodiments of a cannula as described above may be used with the present method and are shown generally in FIGS. 6–13. The present cannula is hollow and is in fluid communication with a connector that can be received by a standard syringe which may contain a variety of fluid usable to separate the epithelial layers. One embodiment of a cannulas connected to a syringe, generally identified by the numeral 74, or other pumping systems providing a fluid source is shown in FIG. 6. Syringe 74 includes a cannula 76, a connector 78, and a syringe body 80, which further includes a plunger 82. Cannula 76 includes a proximal end 84, a distal section 86, a distal tip 88, a contact surface 90, an upper surface 91, and a plurality of apertures 92 as shown in FIG. 7. The length of the cannula 76 may range from about 10 millimeters to about 15 millimeters. Apertures 92 are disposed on one lateral surface, relative to contact surface 90 and upper surface 91 of distal section 86 of cannula 76. Preferably, 15 to 25 apertures 92 are utilized for ejection of syringe media. Distal section 86 includes a channel 93 in fluid communication with apertures 92 and syringe body 80 for delivery of fluid to apertures 92. The diameters of apertures 92 range from about 0.05 to about 0.10 millimeter and are spaced about 0.4 millimeter apart along the side of cannula 76. The radius of curvature of cannula 76 is contemplated to range from about 8 millimeters to about 12 millimeters. Distal tip 88 is preferably tapered as shown in FIG. 9 to allow cannula 76 to enter under the epithelium after an incision 28 is made as shown in FIG. 1c. During separation of the epithelial sheet, the syringe plunger 82 may be depressed to eject various media through the plurality of apertures 92 as mentioned above such as air, gel, liquid, to aid in the separation of the epithelial sheet. Distal tip 88 may also include an aperture as illustrated in FIG. 1b for expelling media to create cut 28 in which case cannula 76 will have no apertures 92.

Various embodiments of distal section 86 include multiple cross-sectional geometries; such as, for example, circular, trapezoidal, and oval as shown in FIGS. 8–13. FIG. 8 illustrates a circular embodiment.

Figure 10:
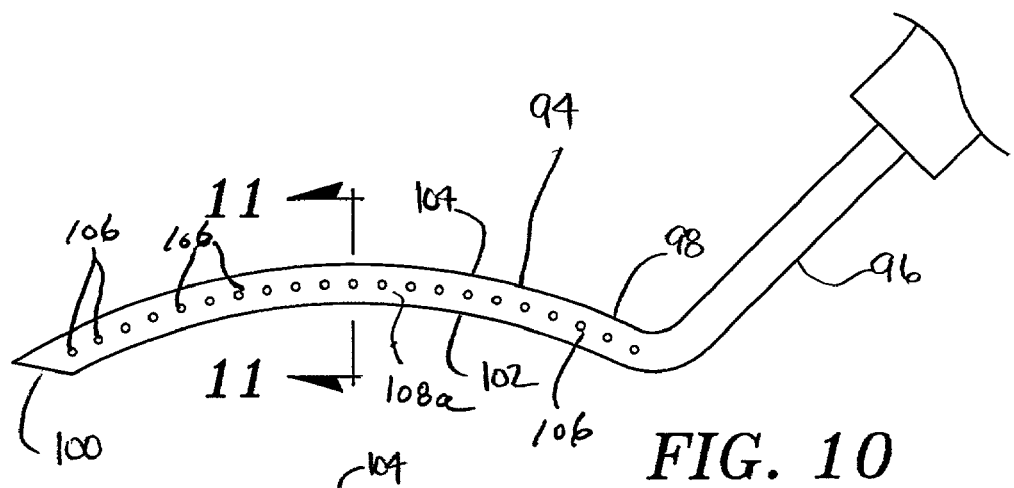
FIG. 10 is a side elevational view of another embodiment of a cannula used in the practice of the present method.
Figure 11:
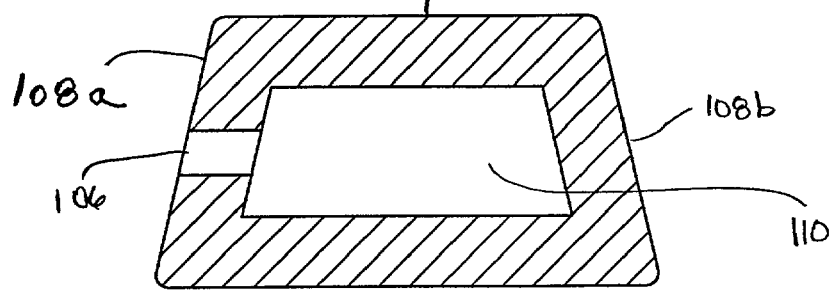
FIG. 11 is a sectional view taken generally along sectional lines 11—11 of FIG. 10 of the cannula of the present invention.

An embodiment of a trapezoidal geometry of the present cannula is shown in FIGS. 10 and 11. A trapezoidal cannula, generally identified by the numeral 94, includes a proximal end 96, a distal section 98, a distal tip 100, a contact surface 102, an upper surface 104, a plurality of apertures 106, sides 108a and 108b, and a channel 110. The width of upper surface 104, for example, in the range from about 0.5 millimeters to about 1.0 millimeters and the width of contact surface 102 to range from 0.75 millimeter to about 1.25 millimeter. The height of the trapezoid, i.e. the distance between contact surface 102 and upper surface 104 is to range from about 0.25 millimeters to about 0.5 millimeters. The length of the cannula 94 may range from about 10 millimeters to about 15 millimeters. The plurality of apertures 106 are disposed on one lateral surface, relative to contact surface 102, of distal section 98 of cannula 94. Preferably, 15 to 25 apertures 106 are utilized for ejection of syringe media. The diameter of apertures 106 ranges from about 0.05 to about 0.10 millimeter and are spaced about 0.4 millimeter apart along the side 108a of cannula 94. The radius of curvature of cannula 94 is contemplated to range from about 8 millimeters to about 12 millimeters. Proximal end 84 is oriented with respect to distal section 86 to form a vertical angle that is in the range of about 40 degrees to about 60 degrees.

Figure 12:
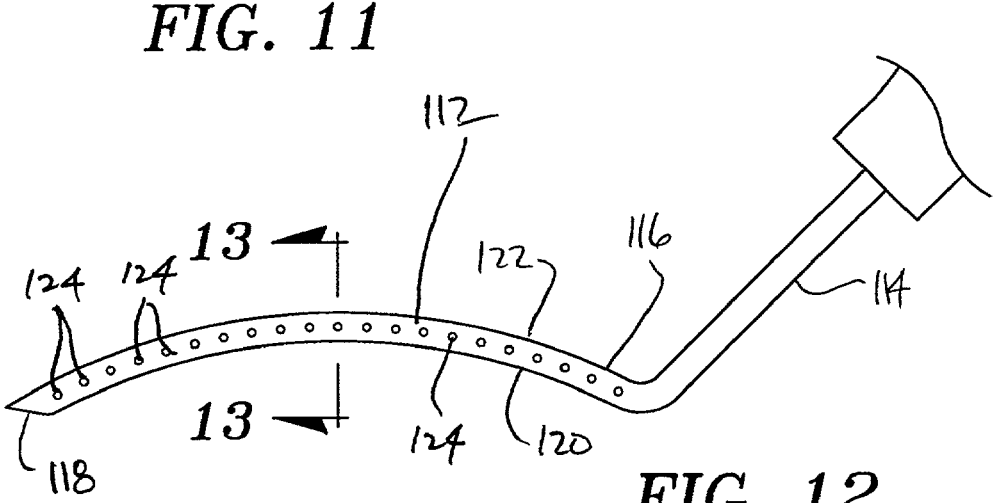
FIG. 12 is a side elevational view of another embodiment of a cannula used in the practice of the present method.
Figure 13:
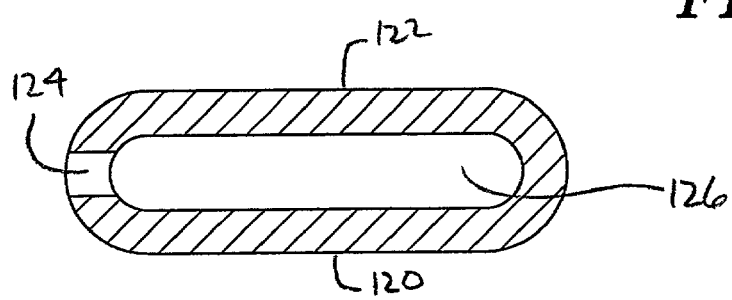
FIG. 13 is a sectional view taken generally along sectional lines 13—13 of FIG. 12 of the cannula of the present invention.

An embodiment of an oval geometry of the present cannula is shown in FIGS. 12 and 13. An oval cannula generally identified by the numeral 112 includes a proximal end 114, a distal section 116, a distal tip 118, a contact surface 120, an upper surface 122, a plurality of apertures 124, and a channel 126. The short axis of the oval ranges in length from about 0.27 millimeters to about 0.5 millimeters and the long axis ranges in length from about 0.75 millimeters to about 1.25 millimeters. During use the short axis is perpendicular to the corneal surface. The length of oval cannula 112 ranges, for example, from about 10 millimeters to about 15 millimeters. The plurality of apertures 124 are disposed on one lateral surface, relative to contact surface 120, of distal section 116 of cannula 112. Preferably, 15 to 25 apertures 124 are utilized for ejection of syringe media. The diameter of apertures 124 ranges from about 0.05 to about 0.10 millimeter and are spaced about 0.4 millimeter apart along the side of cannula 112. The radius of curvature of cannula 112, for example, in the range from about 8 millimeters to about 12 millimeters. Proximal end 114 is oriented with respect to distal section 116 to form a vertical angle that is in the range of about 40 degrees to about 60 degrees.

To accomplish step 40 (FIG. 1a), the separation of the corneal surface epithelium from the underlying epithelium, several embodiments of an epithelial separator as described above may be used with the present method, and are shown generally in FIGS. 14–25. An epithelial separator, generally identified by the numeral 128, includes a slender spatula-like portion 130 connected to a handle 132 by a shaft 134. Shaft 134 is oriented with respect to spatula-like portion 130 so that a vertical angle is formed that ranges from about 40 to about 60 degrees.

Spatula-like portion 130 includes a proximal end 136, a distal section 138, a distal tip 140, a contact surface 142, and an upper surface 144. The height of the spatula-like portion 130 is no greater than about 0.5 millimeter and is preferably less than 0.4 millimeter. Various embodiments of distal section 138 include various cross-sectional geometries such as, for example, circular, triangular, and oval, as shown in FIGS. 16–25. A circular embodiment of spatula-like portion 130 is shown in FIG. 16. The circular embodiment of the spatula-like portion has a length between about 10 millimeters to about 15 millimeters and has a radius of curvature of about 8 millimeters to about 12 millimeters. Distal tip 106 is preferably tapered as shown in FIG. 17 to form a leading edge that can enter under the incision into the epithelium in order to separate the epithelium from the corneal bed.

Proximal end 136 is oriented with respect to distal section 138 to form a vertical angle that is in the range of about 40 degrees to about 60 degrees.

Another embodiment of a separator 128 is shown in FIGS. 18–21. A spatula-like portion 146 includes a proximal end 148, a distal section 150, a distal tip 152, a contact surface 154, and an upper surface 156. Spatula-like portion 146 includes a triangular cross-sectional shape and is shown in FIG. 20, which is a section through sectional lines 20—20 of FIG. 19. Spatula-like portion 146 is triangular in cross-section having a height, generally, of no more than about 0.5 millimeter, and a base of about 1 millimeter, and with the base angles being acute and equal, each preferably less than about 30 degrees. The base, in reference to the triangular cross-section, lies substantially adjacent to the underlying cornea during separation of the epithelium from the corneal bed. The triangular embodiment of the spatula-like portion 146 has a length between about 10 millimeters to about 15 millimeters having a radius of curvature of about 10 millimeters to about 40 millimeters. Shown in FIG. 21, distal tip 152 of the triangular embodiment tapers to contact surface 154 to form leading edge 158. The tip 152 of the spatula-like portion 146 is preferably angled having a chisel-like appearance so that the height of the spatula-like portion 146 tapers forward to the base to form leading edge 158 that has a narrower profile than the rearward section of the spatula. Such leading zone permits the spatula-like portion 146 to be inserted between the layers so that the rest of the spatula 146 can further separate the epithelial layers as the spatula-like portion 146 is moved further under the sheet of epithelium. Proximal end 148 is oriented with respect to distal section 150 to form a vertical angle that is in the range of about 40 degrees to about 60 degrees.

Another embodiment of a separator 128 is shown in FIGS. 22–25. A spatula-like portion 160 includes a proximal end 162, a distal section 164, a distal tip 166, a contact surface 168, and an upper surface 170. Spatula-like portion 160 is shown in FIG. 24, which is a section through sectional lines 24—24 of FIG. 23. In the oval embodiment of spatula-like portion 160 the short-axis ranges in length from about 0.27 millimeters to about 0.5 millimeters and the long-axis ranges in length from about 0.75 millimeters to about 1.25 millimeters. The short axis is perpendicular to contact surface 168 and the long-axis is parallel to the contact surface 168. As shown in FIG. 25, distal tip 166 tapers to form leading edge 172 so that the leading edge may enter into under the epithelium and be used to separate the epithelium from the underlying corneal bed. Proximal end 162 is oriented with respect to distal section 164 to form a vertical angle that is in the range of about 40 degrees to about 60 degrees.

Therefore, it can be seen that the present invention provides for a method and surgical instruments for creating and lifting a sheet of epithelium without killing the tissue or exposing the cornea and eye to dangerous toxins.

Whereas it is intended that the description of the present invention includes several embodiments for implementing the invention. Variations in the description likely to be conceived by those skilled in the art still fall within the breadth and scope of the disclosure of the present invention.

It is also understood that additional applications of the present invention will be apparent to those skilled in the art upon a reading of the description and a consideration of the appended claims and drawings.

The invention claimed is:

1. A surgical instrument for use in corneal reconstruction, comprising:
    a connecting end; and
    a hollow spatula-like member having a proximal end supported by said connecting end and a distal tip opposite said proximal end, said spatula-like member including an arcuate distal section formed in a plane along a curvature, and further including a fluid passageway therein, said fluid passageway being in fluid communication with a fluid source, with one side of said spatula-like member further including a plurality of apertures wherefrom fluid from said fluid source may be ejected,
    wherein said spatula-like member has a trapezoidal cross-sectional shape, and
    wherein said surgical instrument is adapted to separate corneal surface epithelium from the underlying cornea.

2. The surgical instrument of claim 1 wherein said distal tip includes an aperture whereby fluid from said fluid source may be ejected onto the cornea.

3. The surgical instrument of claim 1 wherein said fluid source is a syringe connected to said connecting end.

4. The surgical instrument of claim 1 wherein said spatula-like member has a height of no greater than about 0.5 millimeters.

5. The surgical instrument of claim 1 wherein said distal section has a length of about 10 millimeters to about 15 millimeters.

6. The surgical instrument of claim 1 wherein there are 15 to 25 apertures.

7. The surgical instrument of claim 1 wherein the diameter of said apertures ranges from about 0.05 millimeters to 0.10 millimeters.

8. The surgical instrument of claim 1 wherein the apertures are evenly spaced about 0.4 millimeters apart along said side.

9. The surgical instrument of claim 1 wherein said distal section curvature has a radius of curvature between about 8 millimeters and about 12 millimeters.

10. The surgical instrument of claim 1 wherein said proximal end is oriented with respect to the distal section to form a vertical angle of about 40 degrees to about 60 degrees.

11. The surgical instrument of claim 1 wherein said trapezoidal spatula-like member has a top side and an opposing contact side, said top side having a width of about 0.5 millimeters to about 1.0 millimeters, and said contact side having a width of about 0.75 millimeters to about 1.25 millimeters.

12. The surgical instrument of claim 1 wherein said distal section curvature has a radius of curvature between about 8 millimeters and about 11.5 millimeters.

* * * * *